US011369301B2

(12) United States Patent
Wittenberger et al.

(10) Patent No.: US 11,369,301 B2
(45) Date of Patent: Jun. 28, 2022

(54) HIGHLY FLEXIBLE MAPPING AND TREATMENT DEVICE

(71) Applicant: Medtronic CryoCath LP, Toronto (CA)

(72) Inventors: Dan Wittenberger, L'ile Bizard (CA); Claudia Lueckge, L'ile Bizard (CA)

(73) Assignee: Medtronic CryoCath LP

( * ) Notice: Subject to any disclaimer, the term of this patent is extended or adjusted under 35 U.S.C. 154(b) by 965 days.

(21) Appl. No.: 15/418,264

(22) Filed: Jan. 27, 2017

(65) Prior Publication Data

US 2018/0214045 A1 Aug. 2, 2018

(51) Int. Cl.
*A61B 5/287* (2021.01)
*A61B 5/283* (2021.01)
(Continued)

(52) U.S. Cl.
CPC .............. *A61B 5/287* (2021.01); *A61B 5/063* (2013.01); *A61B 5/283* (2021.01); *A61B 5/6853* (2013.01)

(58) Field of Classification Search
CPC ........... A61B 2018/00005; A61B 2018/00023; A61B 2018/042; A61B 2018/065;
(Continued)

(56) References Cited

U.S. PATENT DOCUMENTS 5,398,683 A * 3/1995 Edwards ................ A61B 5/287
607/116
5,991,650 A * 11/1999 Swanson ............... A61B 5/0422
374/E1.005

(Continued)

FOREIGN PATENT DOCUMENTS

CN 105636538 A 6/2016
CN 105658163 A 6/2016

OTHER PUBLICATIONS

International Search Report and Written Opinion dated Apr. 16, 2018, for corresponding International Application No. PCT/CA2018/050101; International Filing Date: Jan. 29, 2018 consisting of 8-pages.

(Continued)

*Primary Examiner* — Eun Hwa Kim
(74) *Attorney, Agent, or Firm* — Christopher & Weisberg, P.A.

(57) ABSTRACT

A device and system for providing mapping and treatment capabilities without increasing stiffness of the device. An embodiment of a device may include a flexible elongate body and at least one mapping element on the distal portion of the elongate body. Each mapping element may be an area of thermally conductive material, such as metallic nanoparticles, that is embedded within, integrated with, or deposited on the elongate body. The flexibility of the areas of thermally conductive material is at least substantially the same as that of the elongate body so the device may include many electrodes without compromising flexibility and maneuverability of the device. Alternatively, the device may include a treatment element coupled to the elongate body, such as a balloon. The mapping elements may be embedded within, integrated with, or deposited on the balloon and may have at least substantially the same flexibility as that of the balloon.

8 Claims, 6 Drawing Sheets

(51) Int. Cl.
*A61B 5/06* (2006.01)
*A61B 5/00* (2006.01)

(58) Field of Classification Search
CPC ...... A61B 2018/068; A61B 2018/6852; A61B 2018/6853; A61B 2018/6855; A61B 2018/6857; A61B 2562/0271; A61B 2018/0022; A61B 2018/1497
See application file for complete search history.

(56) References Cited

U.S. PATENT DOCUMENTS

| | | | |
|---|---|---|---|
| 6,001,095 A * | 12/1999 | de la Rama | A61N 1/056 606/41 |
| 6,134,463 A * | 10/2000 | Wittkampf | A61B 18/1492 606/41 |
| 6,208,881 B1 | 3/2001 | Champeau | |
| 6,477,396 B1 * | 11/2002 | Mest | A61B 18/1492 606/41 |
| 7,879,029 B2 * | 2/2011 | Jimenez | A61B 18/1492 606/34 |
| 9,101,734 B2 * | 8/2015 | Selkee | A61M 25/0136 |
| 9,119,600 B2 * | 9/2015 | Richardson | A61B 90/00 |
| 9,370,311 B2 | 6/2016 | Stewart et al. | |
| 10,034,707 B2 * | 7/2018 | Papaioannou | A61B 5/0422 |
| 2003/0159700 A1 * | 8/2003 | Laufer | A61B 18/00 128/898 |
| 2008/0294158 A1 * | 11/2008 | Pappone | A61B 18/1492 606/41 |
| 2010/0036376 A1 * | 2/2010 | Anderson | A61N 1/056 606/41 |
| 2010/0204560 A1 | 8/2010 | Salahieh et al. | |
| 2011/0277803 A1 * | 11/2011 | Grande | G01K 13/002 136/225 |
| 2012/0035601 A1 * | 2/2012 | Wittenberger | A61B 18/02 606/21 |
| 2015/0018809 A1 | 1/2015 | Mihalik | |
| 2015/0018818 A1 | 1/2015 | Willard et al. | |
| 2015/0265339 A1 | 9/2015 | Lindquist et al. | |
| 2015/0352326 A1 * | 12/2015 | Tegg | A61B 18/1492 604/95.04 |
| 2015/0366608 A1 * | 12/2015 | Weber | A61B 18/1492 606/41 |
| 2017/0009920 A1 * | 1/2017 | Canatella | F16L 37/0985 |
| 2018/0000542 A1 * | 1/2018 | Oliverius | A61B 18/1492 |
| 2018/0064359 A1 * | 3/2018 | Pranaitis | A61B 18/1492 |
| 2018/0199981 A1 * | 7/2018 | Sheets | A61B 1/00087 |

OTHER PUBLICATIONS

Dumas III, John Hicks, Myocardial Electrical Impedance as a Metric of Completeness for Radiofrequency Ablation Lesions, University of North Carolina, Chapel Hill, 2007.
European Patent Office, Supplementary European Search Report for corresponding European Application No. EP 18 74 4968, dated Sep. 11, 2020, 6 pages.
China National Intellectual Property Administration, Notice on the First Office Action for corresponding Application No. 201880008667. 2, dated Jul. 1, 2021, 20 pages.

* cited by examiner

HIGHLY FLEXIBLE MAPPING AND TREATMENT DEVICE

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a device, system, and method for providing mapping functionality to a device without compromising the flexibility of the device's distal portion.

BACKGROUND

Cardiac arrhythmias are conditions in which the heart's normal rhythm and cardiac efficiency is disrupted, typically due to a presence of aberrant electrical current(s) propagating through the myocardial tissue. The efficacy of many currently used arrhythmia treatments requires a very precise localization of the treatment target (for example, an area of target tissue through which the aberrant electrical current is propagated) prior to the delivery of treatment.

Whether the treatment involves delivering a drug, applying a form of energy to the target, removing energy from the target, or mechanically affecting the target tissue, the exact location of the target must be known. Standard imaging techniques are available and can be used when the target can be visualized, such as by fluoroscopy, ultrasound, computed tomography (CT), magnetic resonance imaging (MRI), or the like. In some cases, the location of the target is not visual, but rather relies on the identification of the electrical properties of the tissue substrate.

In some types of arrhythmia, the propagating electrical current through the myocardium is used to guide the electrophysiologist to the exact location to be treated. Generally, this is accomplished by a high-density electrical mapping of a portion of the heart or the entire heart. Various maps can be generated using voltage, frequency, activation maps, or the like. These maps are commonly overlaid on a 3D reconstruction of the heart developed using one of the visualization techniques discussed above.

While most visualization techniques are passive, in the sense that the technique itself does not mechanically interact with the geometry of the tissue being visualized and therefore does not distort the anatomy, most electrical mapping techniques do require mechanical contact between the mapping catheter (or array) and the myocardium.

Most catheters or mapping arrays have one or more flexible members that carry metal electrodes connected to wires that return electrical signals from the myocardium to an acquisition and processing system. The flexibility of the members determines the distortion that is inflicted upon the mapped area in the process. Even highly flexible members, such as those made of soft polymers, are affected by the presence of metallic electrodes, typically platinum-iridium (PtIr) bands attached to the surface of the flexible members. These electrodes are generally non flexible and cause a stiffening of the area of the device on which they are installed. Additionally, in most cases the electrode rings or bands are swaged on the flexible member, causing compressing of the polymeric support, thus further reducing flexibility. Adhesives used under or at the edges of the electrode bands, as well as the numerous wires running through the member, also contribute to its stiffness.

Additionally, some combination mapping and ablation devices include mapping electrodes on an external surface of an expandable element, such as a cryoballoon. In this case, the mapping electrode wires are often fed through the balloon, thereby presenting a risk that the wires should weaken or otherwise compromise the integrity of the balloon. Such a configuration therefore risks rupture of the balloon and, potentially, leakage of the fluid within the balloon into the patient's body.

SUMMARY

Some embodiments advantageously provide a device with mapping and treatment capabilities without compromised flexibility. In one embodiment, a medical device may include a distal portion including at least one treatment element having a first flexibility and at least one mapping element, the at least one mapping element being an area of thermally conductive material having a second flexibility that is at least substantially the same as the first flexibility.

In one aspect of the embodiment, the thermally conductive material may include nanoparticles. For example, the nanoparticles may be metallic nanoparticles. In one aspect of the embodiment, the metallic nanoparticles may be composed of at least one of platinum and platinum-iridium.

In one aspect of the embodiment, the distal portion may further include at least one tracing in communication with each of the at least one mapping element, each of the at least one tracing being composed of a thermally conductive material. In one aspect of the embodiment, each of the at least one tracing may have a third flexibility that is at least substantially the same as the first and second flexibilities. In one aspect of the embodiment, the at least one tracing in communication with each of the at least one mapping element may include a first tracing composed of a first metal and a second tracing composed of a second metal, the first and second tracings being a thermocouple. In one aspect of the embodiment, the first metal may be one of gold and palladium, and the second metal may be platinum.

In one aspect of the embodiment, the medical device may further include an elongate body, the distal portion being a distal portion of the elongate body, the at least one mapping element being an area of thermally conductive material that is incorporated into the elongate body. In one aspect of the embodiment, the elongate body may have a circumference, each of the at least one mapping elements extending around less than an entirety of the circumference.

In one aspect of the embodiment, the at least one treatment element may include an expandable treatment element, the at least one mapping element being an area of thermally conductive material that is incorporated into the expandable treatment element. In one aspect of the embodiment, the thermally conductive material may include metallic nanoparticles. In one aspect of the embodiment, the distal portion may further include at least one tracing in communication with each of the at least one mapping element, each of the at least one tracing being incorporated into the expandable element. In one aspect of the embodiment, each of the at least one tracing may be composed of a thermally conductive material.

In one embodiment, a medical system may include a medical device including an elongate body having a first flexibility and at least one mapping element on the elongate body, the at least one mapping element being an area of thermally conductive material having a second flexibility that is at least substantially the same as the first flexibility. The medical system may further include a control unit in communication with the medical device.

In one aspect of the embodiment, each of the at least one mapping elements may include a thermocouple that is in communication with the control unit, each thermocouple including a first tracing composed of nanoparticles of a first metal and a second tracing composed of nanoparticles of a second metal, each of the first and second tracings being embedded within the elongate body. In one aspect of the embodiment, each of the first tracing and the second tracing of each thermocouple may have a third flexibility that is at least substantially the same as the first and second flexibilities. In one aspect of the embodiment, the elongate body may have a circumference, each of the at least one mapping elements extending around less than an entirety of the circumference to define a gap in the mapping element. In one aspect of the embodiment, the at least one mapping element may include a plurality of mapping elements spaced apart from each other and extending along a distance of the elongate body in a distal-to-proximal direction, the first and second tracings of each thermocouple extending in the distal-to-proximal direction through the gap of the next proximal mapping element.

In one embodiment, a medical system may include: a medical device including: an elongate body having a flexibility and an at least substantially continuous circumference; a plurality of electrodes on the elongate body that are configured to record at least one impedance measurement, each of the plurality of electrodes being an area of thermally conductive nanoparticles of a first metal, each of the plurality of electrodes having a flexibility that is at least substantially the same as the flexibility of the elongate body, each of the plurality of mapping elements extending around less than an entirety of the circumference of the elongate body; and a plurality of tracings in electrical communication with the plurality of mapping elements, each of the plurality of tracings being an area of thermally conductive nanoparticles of at least one of the first metal, a second metal, and a third metal; and a control unit in communication with the medical device and configured to receive the at least one impedance measurement from the plurality of electrodes and to assess a formation of a lesion in an area of tissue based on the at least one impedance measurement.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
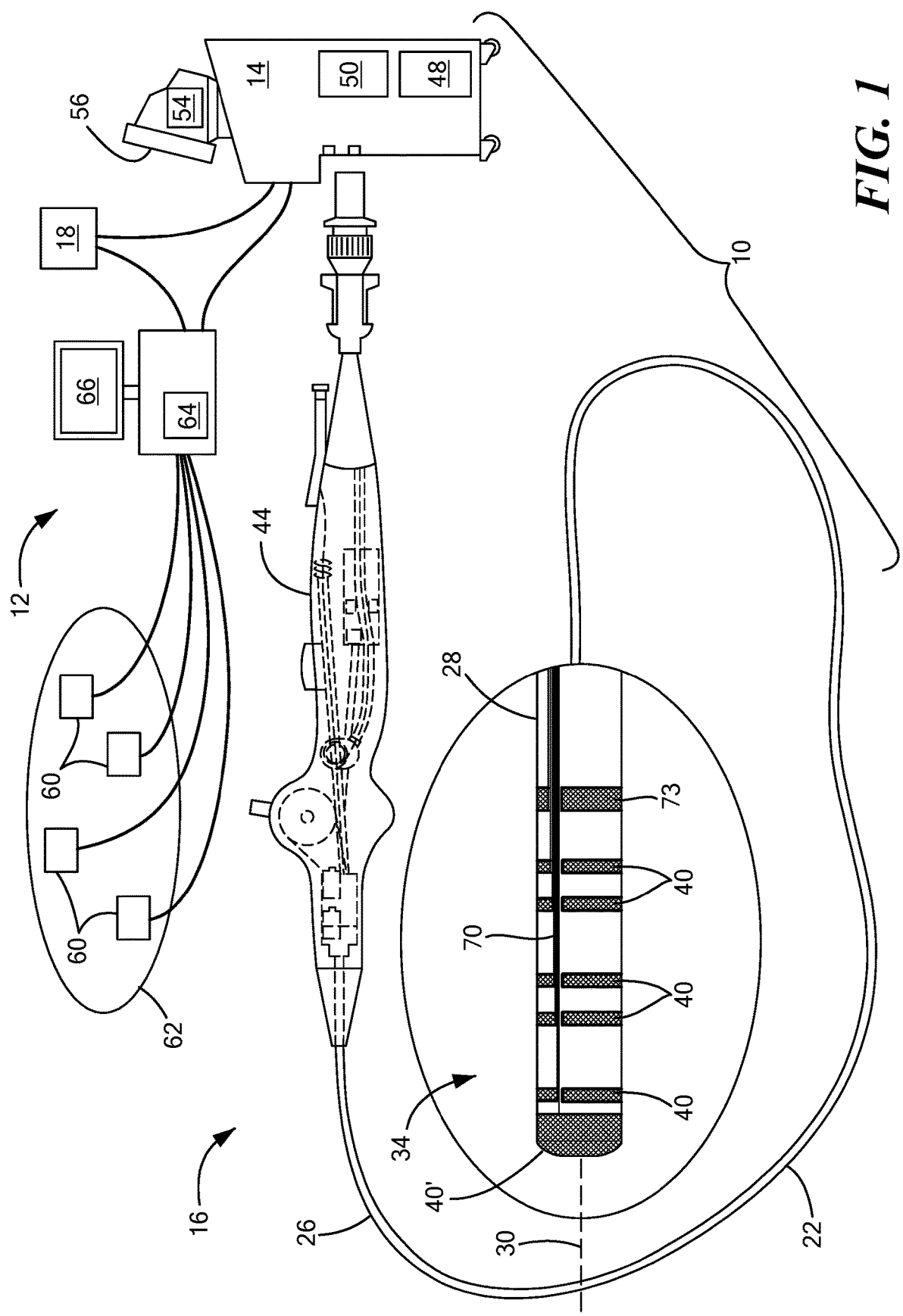
FIG. 1 shows an exemplary medical system including a medical device.

The device described herein has mapping and treatment capabilities without compromising flexibility of the distal portion of the device. Before describing in detail exemplary embodiments, it is noted the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 2:
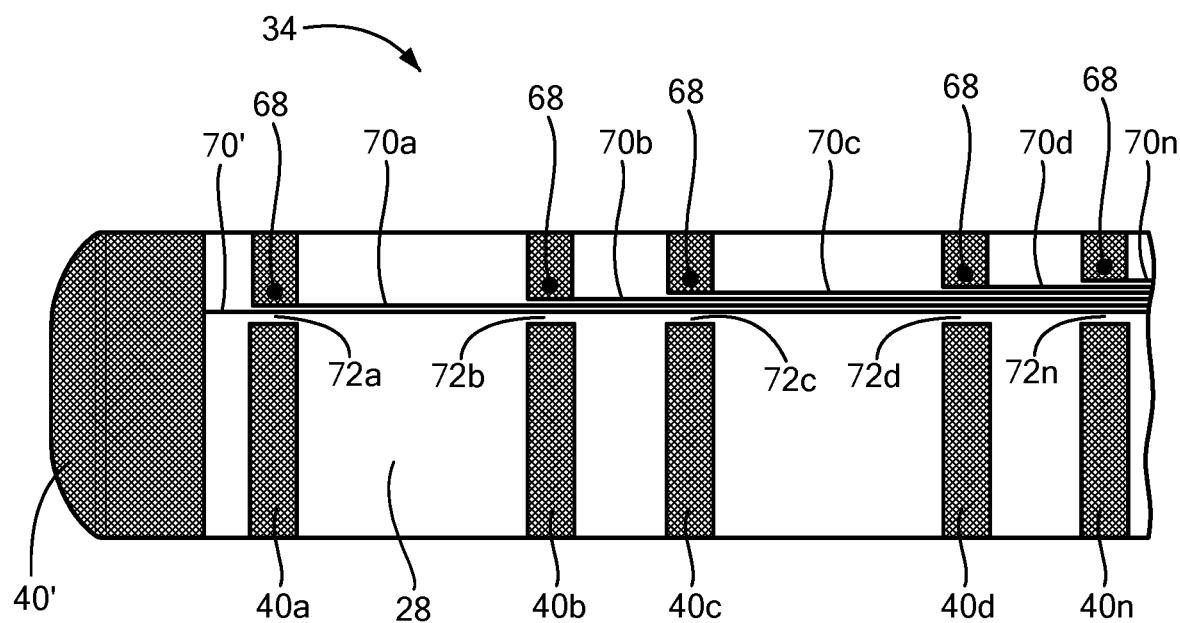
FIG. 2 shows a close-up view of a distal portion of the medical device of FIG. 1.

Referring now to the drawing figures in which like reference designations refer to like elements, an embodiment of a medical system is shown in FIGS. 1 and 2, generally designated as "10." One embodiment of the system 10 may include a navigation system 12, although the system 10 may also include a control unit 14 or operating console and a medical device 16 in communication with the navigation system 12 and the control unit 14. The system 10 may further include an imaging system 18 for obtaining images of anatomical features within a patient.

The medical device 16 may be a treatment and/or mapping device. The medical device 16 may include an elongate body 22 passable through a patient's vasculature and/or proximate to a tissue region for diagnosis or treatment. For example, the device 16 may be a catheter that is deliverable to the tissue region via a sheath or intravascular introducer (not shown) or a device that can access the pericardial space. The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28. The elongate body 22 may further define a circumference, which may be an at least substantially continuous circumference (for example, as shown in FIG. 1).

The medical device 16 may further include one or more treatment elements 34 at, coupled to, or on the elongate body distal portion 28 for energetic, therapeutic, and/or investigatory interaction between the medical device 16 and a treatment site or region. The treatment region element(s) 34 may deliver, for example, cryogenic therapy, radiofrequency energy, ultrasound energy, laser energy, or other energetic transfer with a tissue area in proximity to the treatment element(s), including cardiac tissue. For example, the treatment element(s) 34 may include thermally transmissive regions in thermal communication with a coolant or heat source, thermally transmissive regions in electrically communication with a power source, surface therapeutic elements such as surface radiofrequency electrodes, or the like. Additionally, the device 16 may include more than one type of treatment element 34. Further, if the device includes one or more treatment electrodes, each treatment electrode 34 may be considered to be a treatment element 34. In the exemplary system embodiment shown in FIG. 1, the device 16 may include a treatment element 34 that is non-expandable. The non-expandable elongate body distal portion 28 may function as a treatment element, such as when a portion of the distal portion 28 is electrically conductive, thermally conductive, transmits laser energy, ultrasound energy, or the like, and/or within which a coolant circulates that lowers the temperature of the distal portion 28. Additionally or alternatively, the non-expandable distal portion 28 may include one or more treatment elements 34 configured for energy transfer, such as electrodes in communication with an energy source. In the embodiment shown in FIG. 1, the elongate body distal portion 28 may function as a treatment element 34 for energy transfer and may include a plurality of mapping electrodes 40. Alternatively, the plurality of electrodes 40 may be configured for both mapping and the delivery of treatment energy. Further, the plurality of electrodes 40 may also be configured to record impedance measurements from the tissue for lesion assessment.

Figure 7:
FIG. 7 shows an exemplary location of a medical device during a treatment procedure.

The elongate body distal portion 28 may be flexible. For example, the distal portion 28 may be transitionable between an at least substantially linear first configuration and a curvilinear, looped, or otherwise expanded second configuration (for example, as shown in FIG. 7). However, it will be understood that any of a myriad of mapping and energy transfer configurations may be used.

Figure 8:
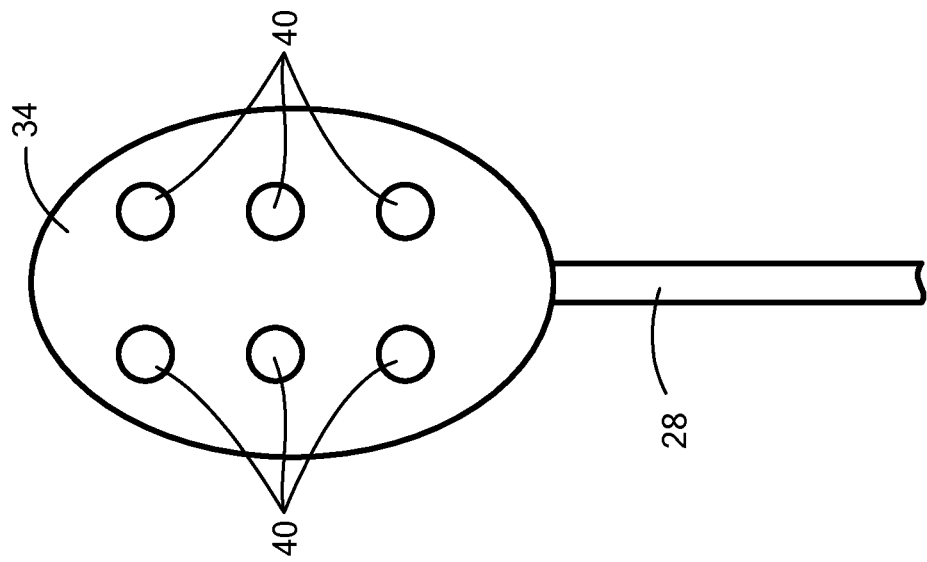
FIG. 8 shows a further embodiment of a distal portion of a medical device.
Figure 10:
FIG. 10 shows a further exemplary location of a medical device during a treatment procedure.
Figure 9:
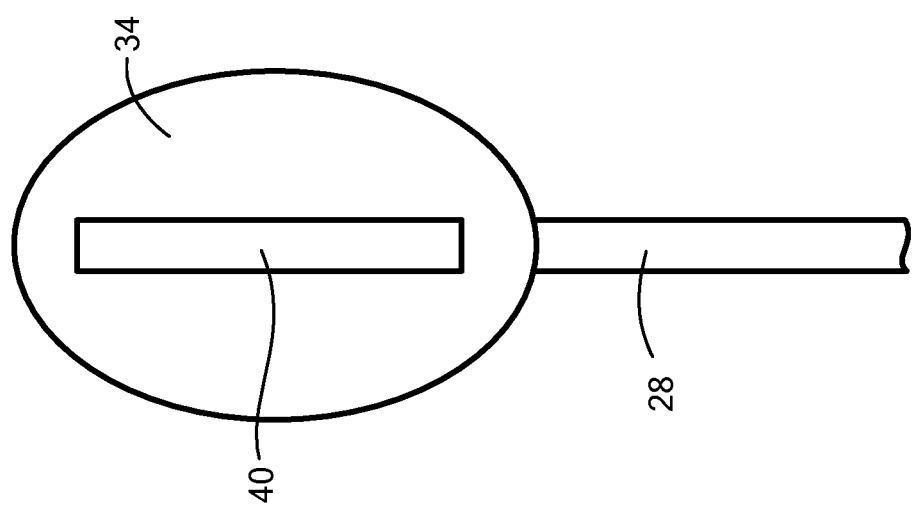
FIG. 9 shows a further embodiment of a distal portion of a medical device.

In another embodiment, the device 16 may include an expandable treatment element 34, such as one or more balloons. The expandable treatment element 34 may be coupled to a portion of the elongate body distal portion 28 (for example, as shown in FIGS. 8-10). The expandable treatment element 34 may further include one or more material layers providing for puncture resistance, radiopacity, or the like. If the device 16 is used to delivery cryotherapy (or if used with another energy modality that requires fluid to be delivered to the inner chamber of the treatment element 34), the device may also include one or more fluid injection elements. The device 16 may also include one or more treatment elements in communication with an energy source, such as one or more electrodes in communication with a source or radiofrequency energy. Further, the device 16 may include one or more mapping electrodes 40. Alternatively, the device 16 may include an expandable element that is not used for energy transfer, but is instead expanded or inflated to support and bring into contact with tissue the mapping electrodes 40 and/or treatment elements 34 (for example, electrodes).

Alternatively, the expandable treatment element 34 may include at least one carrier arm bearing one or more treatment electrodes (not shown).

The one or more mapping electrodes 40 may be used by the navigation system 12 to visualize the device 16 on a control unit display and/or a navigation system display. Further, each mapping electrode 40 and treatment element 34 in communication with a power source may be electrically conductive segments for conveying an electrical signal, current, or voltage to a designated tissue region and/or for measuring, recording, receiving, receiving, assessing, or otherwise using one or more electrical properties or characteristics of surrounding tissue or other electrodes. The electrodes may be configured in a myriad of different geometric configurations or controllably deployable shapes, and may also vary in number to suit a particular application, targeted tissue structure or physiological feature.

Although not shown, the system 10 may include one or more sensors to monitor the operating parameters throughout the system, including for example, pressure, temperature, flow rates, volume, power delivery, impedance, or the like in the control unit 14 and/or the medical device 16, in addition to monitoring, recording or otherwise conveying measurements or conditions within the medical device 16 or the ambient environment at the distal portion of the medical device 16. The sensor(s) may be in communication with the control unit 14 for initiating or triggering one or more alerts or therapeutic delivery modifications during operation of the medical device 16. One or more valves, controllers, or the like may be in communication with the sensor(s) to provide for the controlled dispersion or circulation of fluid through the lumens/fluid paths of the medical device 16. Such valves, controllers, or the like may be located in a portion of the medical device 16 and/or in the control unit 14.

The medical device 16 may include a handle 44 coupled to the elongate body proximal portion 26. The handle 44 may include circuitry for identification and/or use in controlling of the medical device 16 or another component of the system. Additionally, the handle 44 may also include connectors that are mateable to the control unit 14 to establish communication between the medical device 16 and one or more components or portions of the control unit 14. The handle 44 may also include one or more actuation or control features that allow a user to control, deflect, steer, or otherwise manipulate a distal portion of the medical device 16 from the proximal portion of the medical device 16. For example, the handle 44 may include one or more components such as a lever or knob for manipulating the elongate body 22 and/or additional components of the medical device 16.

As used herein, the term "control unit 14" for simplicity may include any system components that are not part of the medical device 16 itself, other than components of the navigation system 12 and the imaging system 18, regardless of whether the component is physically located within or external to the control unit 14. Further, the navigation system 12 may be a standalone system in communication with the control unit 14 or may be contained within or integrated with the control unit 14, even though it is shown as being physically separated from the control unit in FIG. 1. The control unit 14 may include one or more components for the delivery of one or more energy modalities for which the system is used. For example, if the system 10 is used to deliver cryotherapy, the control unit 14 may include a supply 48 of a fluid such as a coolant, cryogenic refrigerant, or the like, an exhaust or scavenging system for recovering or venting expended fluid for re-use or disposal, as well as various control mechanisms. In addition to providing an exhaust function for the fluid or coolant supply 48, the control unit 14 may also include pumps, valves, controllers or the like to recover and/or re-circulate fluid delivered to the handle 50, the elongate body 22, and/or the fluid pathways of the medical device 16. Further, a vacuum pump in the control unit 14 may create a low-pressure environment in one or more conduits within the medical device 16 so that fluid is drawn into the conduit(s)/lumen(s) of the elongate body 22, away from the distal portion 28 and towards the proximal portion 26 of the elongate body 22. Additionally or alternatively, the control 14 unit may include an energy source 50 as a treatment or diagnostic mechanism in communication with the treatment element(s) 34 of the medical device 16. As a non-limiting example, the energy source 50 may be a radiofrequency generator having a plurality of output channels, with each channel coupled to an individual treatment electrode 34. The radiofrequency generator 50 may be operable in one or more modes of operation.

The control unit 14 may further include one or more controllers, processors, and/or software modules 54 containing processing circuitry configured to execute instructions or algorithms to provide for the automated operation and performance of the features, sequences, calculations, or procedures described herein and/or required for a given medical procedure. In one embodiment, the processing circuitry may include a processor and a memory. The memory may be in electrical communication with the processor and have instructions that, when executed by the processor, configure the processor to receive, process, or otherwise use signals from the device 16. Further, the control unit 14 may include one or more user input devices, controllers, and displays 56 for collecting and conveying information from and to the user.

The system 10 may optionally include a navigation system 12, which may be any commercially available navigation system suitable for use with the control unit 14, device 16, and type of procedure. As a non-limiting example, the navigation system 12 may include a plurality of navigation electrodes 60, a reference electrode (not shown), and a processing unit 64 that collects and processes signals from the device mapping electrodes 40, and a display 66 that displays to the user the location of the device 12 within the patient's body and/or relative to the target anatomical feature, recommended treatment areas, tissue thickness, or the like. The processing unit 64 may include processing circuitry including a memory and a processor, the memory in communication with the processor and having instructions that, when executed by the processor, configure the processor to perform the calculations and determinations discussed herein. Additionally or alternatively, this information may be displayed on the display 56 of the control unit 14. The navigation system 12 may also include an energy source (not shown) for delivering energy to the plurality of navigation electrodes 60. Alternatively, the navigation system 12 may be in communication with the control unit energy source 50. For example, the processing unit 64 may be configured, programmed, or programmable to perform the calculations and make the determinations discussed in greater detail below to identify an anatomical feature and/or a target location for a medical device. Further, the processing unit 64 may execute software and display a software interface with which the user may interact to make a selection, rotate and flag an image, open folders, control the navigation system 12, or the like. As a non-limiting example, the user may interact with the software interface using a touch screen, a keyboard, a mouse, or other input device.

The navigation electrodes 60, which may also be referred to as surface electrodes, may be applied to the patient's 62 skin and may deliver relatively low-frequency radiofrequency energy through the patient toward the procedure site, current device location, or the target anatomical feature. The mapping electrodes 40 on the device 16 may each record a voltage and impedance from this energy and transmit data to the processing unit 64, which may then determine a position of the mapping electrode 40, and therefore the device 16, within the patient. In addition to impedance-based systems, other navigation electrodes may be used such as magnetic field based, hybrid impedance/magnetic field based, ultrasound field based, and/or radiation based, and/or navigation systems that may be developed in the future. The processing unit 64 may perform this calculation many times during a procedure, frequently updating the registered location and displaying such to the user so the user can visualize the location of the device relative to the target anatomical feature in real time.

The system 10 may optionally include an imaging system 18, which may be a computed tomography (CT) system, a magnetic resonance imaging (MRI) system, or other system suitable for creating images of locations within a patient's body. The imaging system 18 may be in communication with and digitally transmit images to the navigation system 12 and/or the control unit 14 for further processing. Alternatively, images recorded by the imaging system 18 may be recorded and transferred to the navigation system 12 and/or the control unit 14 by a user.

Referring now to FIGS. 1 and 2, the distal portion of an exemplary device is now described in more detail. As noted above, the device 16 may include one or more treatment elements 34 and one or more mapping electrodes 40. In the embodiment shown in FIGS. 1 and 2, at least a portion of the distal portion 28 may function as a treatment element 34, although it will be understood that the mapping electrodes 40 may optionally be used for energy transfer. For example, the distal portion 28 may be thermally conductive and may be in communication with an energy source 50 and/or coolant source 48. Further, each electrode 40 may include a thermocouple 68 for measuring temperature associated with the electrode 40 and/or tissue with which the electrode is in contact.

Each mapping electrode 40 may include one or more conductive "tracings" 70 that function as traditional electrode wires, including the thermocouple wire pairs. However, these tracings do not have a stiffening effect on the elongate body 22 or present safety risks in cryotreatment devices (that is, the tracings are not fed through the expansion chamber), as do traditional electrode wires. For simplicity, each electrode 40 is said to have a tracing 70, regardless of how many tracings are in contact with each electrode. As is shown in detail in FIG. 2, each mapping electrode 40 may be in communication with a distal end of a tracing 70, and each tracing 70 may extend on or within the elongate body 22 from its associated electrode 40 to the handle 44. The proximal end of each tracing 70 may be in communication with the handle 44 and/or the control unit 14. Alternatively, the proximal end of each tracing 70 may be in communication with a scanning/multiplexing module that can transfer signals from the electrodes 40 at very high speed, with or without the use of a physical wired connection to the control unit 14.

Further, each electrode 40 and tracing 70 may be composed of a thermally and/or electrically conductive material, such as conductive nanoparticles. As a non-limiting example, this conductive material may be incorporated into, implanted into, integrated with, and/or deposited on the elongate body 22 in the areas where the electrodes 40 and tracings 70 are located. As a non-limiting example, the nanoparticles may be applied to the surface of the elongate body 22 or the treatment element 34 or doped or otherwise added to the material of the elongate body 22 or the treatment element 34 (or any other component of the device). Further, the areas of conductive material may have a flexibility or compliance that is approximately or at least substantially the same as the flexibility or compliance of the surrounding material, such as that of the elongate body 22. However, it will be understood that the material may be located in areas where a higher level of thermal conductivity than the surrounding elongate body 22 portions is desired. In this case, the areas of conductive material may not be "electrodes" that are in communication with the other system components, but may simply facilitate energy transfer between the device 16 and the adjacent tissue. In such a case, the areas of conductive material could be referred to as treatment elements; however, for simplicity areas of conductive material are herein referred to as electrodes 40.

In addition to preserving the flexibility of the distal portion of the device 16 and thereby avoiding distortion of the anatomy of the tissue being investigated and/or treated, the areas of conductive material also allow for device miniaturization, a single connection of the electrode array to the other system components, and eliminates potential for patient injury caused by sharp or protruding edges of currently known electrodes.

The conductive material may be incorporated into or deposited onto the elongate body 22 such that the areas of conductive material appear as typical band electrodes. However, these electrodes 40 may not extend around the entire circumference of the elongate body 22 and instead may have at least one open portion 72 or gap between the two ends of the electrode 40 through which tracings 70 from distal electrodes 40 may pass. For example, the device 16 may include a distal tip electrode 40'; the other electrodes 40 may be referred to herein as "band" electrodes 40a . . . 40n for simplicity, where "n" represents any number of electrodes greater than 1, despite the presence of the at least one open portion 72 in each electrode 40. The plurality of electrodes 40 may extend along a length or distance of the elongate body 22. The tracing 70' of the distal tip electrode 40' may pass through the open portion 72a of the distalmost band electrode 40a and all of the band electrodes 40b . . . 40n proximal to the distalmost band electrode 40a. The tracing 70a of the distalmost band electrode 40a may pass through the open portion 72b of the next electrode 40b that is proximal to the distalmost band electrode 40a and all of the band electrodes 40c . . . 40n proximal to band electrode 40b. This may continue for "n" electrodes. Further, the proximalmost electrode 40n to the handle 44 may have an open portion 72n that is greater than the open portion 72a of the distalmost electrode 40a in order to allow the tracings 70 of all the electrodes 40 to pass therethrough. Thus, the tracings 70 may extend in a distal-to-proximal direction, toward the handle.

The electrodes 40 may be spaced such that there is a first distance between electrodes 40 in a pair and a second distance between pairs of electrodes 40. As a non-limiting example, electrodes 40b and 40c may be spaced by a first distance of approximately 2 mm and electrodes 40d and 40e (or 40n, as shown in FIG. 2) may also be spaced by the first distance of approximately 2 mm. However, there may be a second distance of approximately 5 mm between the first electrode pair (40b and 40c) and the second electrode pair (40d and 40e/40n). The distalmost electrode 40a may be separated from the distal tip electrode 40' by a third distance that is less than the first and second distances.

Figure 3:
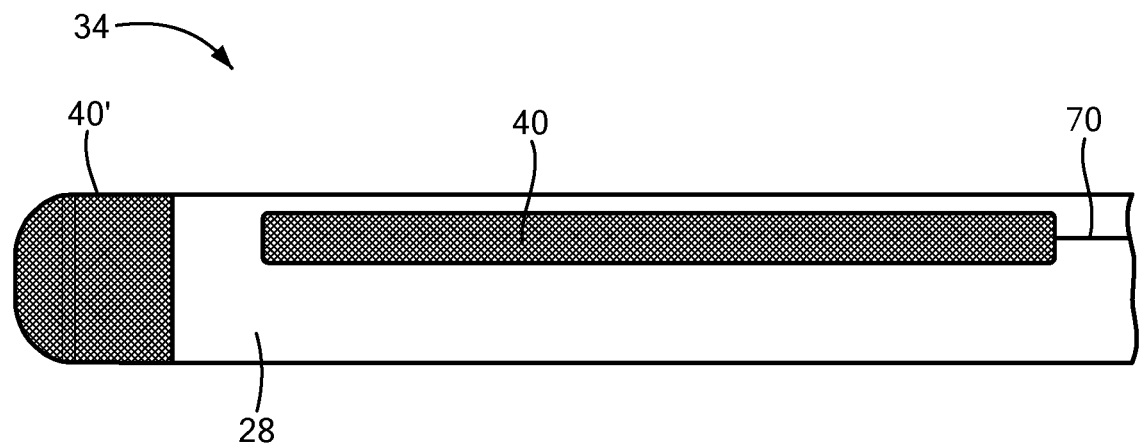
FIG. 3 shows a close-up view of a further embodiment of a distal portion of a medical device.
Figure 4:
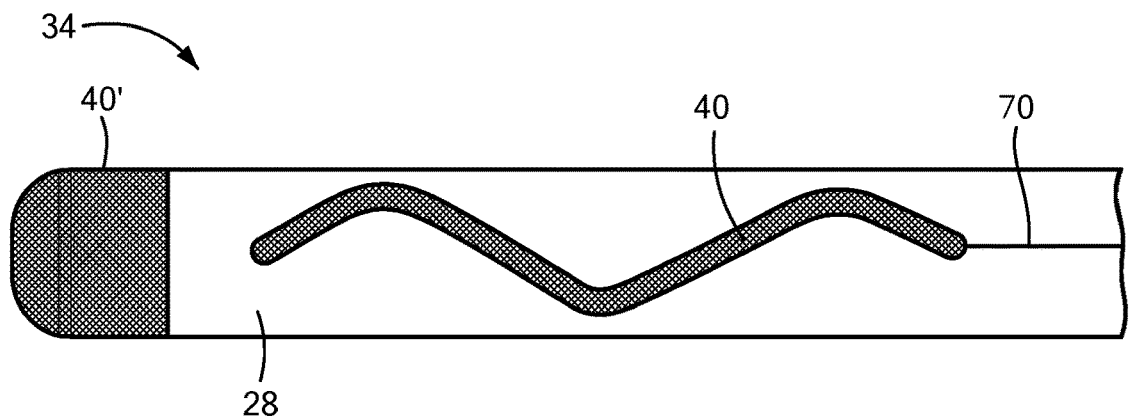
FIG. 4 show a close-up view of a further embodiment of a distal portion of a medical device.
Figure 5:
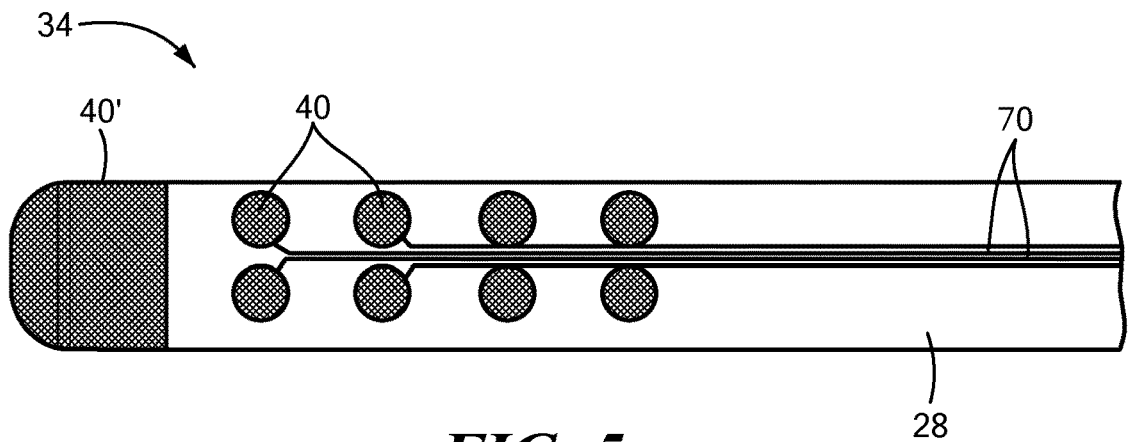
FIG. 5 shows a close-up view of a further embodiment of a distal portion of a medical device.
Figure 6:
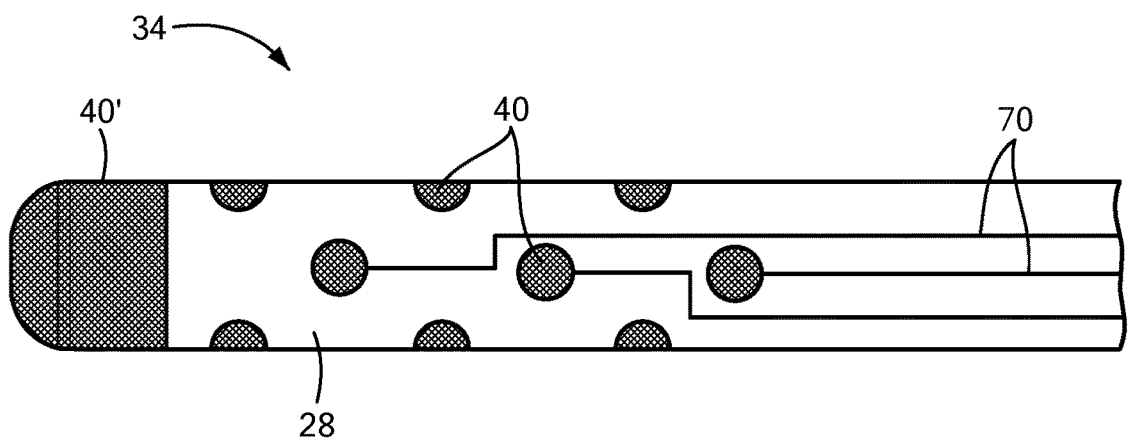
FIG. 6 shows a close-up view of a further embodiment of a distal portion of a medical device.

Alternatively, the electrodes 40 and tracings 70 may have other configurations. As a non-limiting example, the electrodes 40 may be linear (for example, as shown in FIG. 3), serpentine (for example, as shown in FIG. 4), or discrete areas (for example, as shown in FIGS. 5 and 6). Additionally, the tracings 70 may extend toward the elongate body proximal portion 26 in patterns other than or in addition to the linear pattern shown in FIG. 2. For example, the tracings 70 may extend proximally from the electrodes 40 on the elongate body 22 in a spiraling pattern, a fanned pattern, or in any other suitable pattern. Further, the tracings may be in electrical communication with a scanning/multiplexing module that can then transfer signals received through the tracings to the processing unit 64 at very high speed, with or without the use of physical wires.

The depth of implantation (or integration) of the conductive material of the tracings 70 may allow for a continuous construction of the distal portion 28, with no or very little impact on the stiffness of the device. For example, the tracings 70 may be located on the outer surface of the elongate body 22 where they come into direct contact with tissue, or they may be located under the surface of the elongate body 22 where they are not in direct contact with tissue (for example, located within a wall of the elongate body 22).

As discussed above, the electrodes 40 and tracings 70 may be composed of a conductive material such as metal nanoparticles. For example, metals such as platinum (Pt) and/or platinum-iridium (PtIr) may be used to form the electrodes 40, whereas the thermocouple 68 may include an intersection of a gold (Au) tracing and a Pt tracing, or a Pt tracing with a palladium (Pd) tracing.

Referring now to FIG. 7, an embodiment of a medical device positioned in the pericardial space is shown. As a non-limiting example, the distal portion 28 of the device 16 may be inserted into the pericardial space, such as by using subxiphoid access. The distal portion 28 may be transitioned from an at least substantially linear first configuration to an expanded second configuration. Here, the distal portion 28 may be the treatment element 34 (for example, a coolant may be circulated through the distal portion 28 proximate the electrode 40) and may have a looped configuration in the expanded second configuration.

The looped treatment element 34 may be positioned on the heart tissue such that the loop completely (as shown in FIG. 7), or at least partially, encircles an area of target tissue 74. For example, the area of target tissue 74 may be a source of an aberrant electrical current and/or an area of myocardial infarction. Mapping signals, such as electrograms (EGMs) may be recorded by the mapping electrodes 40 from the tissue, and these may be used by the processing unit 64 and/or the control unit 14 to communicate to the user whether the area of target tissue is within the looped treatment element 34. Once it is determined that the treatment element 34 is in the desired location, energy transfer may begin. As a non-limiting example, the control unit 14 may circulate a coolant through the elongate body and within the distal portion 28 that constitutes the treatment element 34. Additionally or alternatively, the treatment element 34 may include one or more treatment electrodes from which treatment energy may be delivered. Treatment energy delivery and/or circulation of coolant may be initiated automatically or semi-automatically by the control unit or manually by the user. Various combinations of unipolar and/or bipolar impedance measurements may then be recorded by the electrodes 40 for lesion assessment and/or to assess an amount of tissue damage. As a non-limiting example, an impedance measurement may be recorded between electrodes 40b and 40d and an impedance measurement may be recorded between electrodes 40a and 40c, or between any of the electrodes 40 and a reference electrode 73. Sufficient lesion formation may be indicated by a reduction in impedance, the amount of reduction depending on the frequency and the electrode surface area (for example, very small electrodes will have a higher impedance than larger electrodes).

Referring now to FIGS. 8 and 9, further embodiments of a medical device is shown. As discussed above, the device 16 may include an expandable element, which may optionally function as a treatment element 34. As a non-limiting example, the system 10 and device 16 may be configured for use for cryotreatment, and the treatment element 34 may be an inflatable balloon through which a coolant may be circulated. As shown in FIGS. 8 and 9, the expandable treatment element 34 may include one or more mapping electrodes 40 that are created using conductive material, such as metal nanoparticles, as discussed above. The conductive material may be incorporated into, implanted into, integrated with, and/or deposited on the treatment element.

In the embodiment shown in FIG. 8, the treatment element 34 may include a plurality of discrete electrodes 40 and each electrode 40 may include a tracing 70. Alternatively, the areas of conductive material may not be in communication with other components of the device, but may simply be used to enhance thermal conductivity as compared to the thermal conductivity of the surrounding expandable treatment element 34, such as may be useful when the device is used in, for example, a cryotreatment procedure.

In the embodiment shown in FIG. 9, the treatment element may include one or more elongate or at least substantially linear electrodes 40, each of which including a tracing 70. Alternatively, the areas of conductive material may not be in communication with other components of the device, but may simply be used to enhance thermal conductivity as compared to the thermal conductivity of the surrounding expandable treatment element 34, as noted immediately above.

Referring now to FIG. 10, an embodiment of a medical device positioned in the pericardial space is shown. As a non-limiting example, the distal portion 28 of the device 16 may be inserted into the pericardial space, such as by using subxiphoid access. The distal portion 28 may be inflated from a deflated first configuration to an expanded second configuration.

The expanded treatment element 34 may be positioned on the heart tissue such that the treatment element 34 completely (as shown in FIG. 10), or at least partially, covers or is in contact with an area of target tissue 74. For example, the area of target tissue 74 may be a source of an aberrant electrical current and/or an area of myocardial infarction. Mapping signals, such as electrograms (EGMs) may be recorded by the mapping electrodes 40 from the tissue, and these may be used by the processing unit 64 and/or the control unit 14 to communicate to the user whether the area of target tissue is within the looped treatment element 34. The electrodes 40 are not visible in FIG. 10, as they are between the treatment element 34 and the tissue. Once it is determined that the treatment element 34 is in the desired location, energy transfer begin. As a non-limiting example, the control unit 14 may circulate a coolant through the treatment element 34. Additionally or alternatively, the treatment element 34 may include one or more treatment electrodes from which treatment energy may be delivered. Treatment energy delivery and/or circulation of coolant may be initiated automatically or semi-automatically by the control unit or manually by the user. Various combinations of bipolar impedance measurements may then be recorded by the electrodes 40 for lesion assessment.

Figure 11:
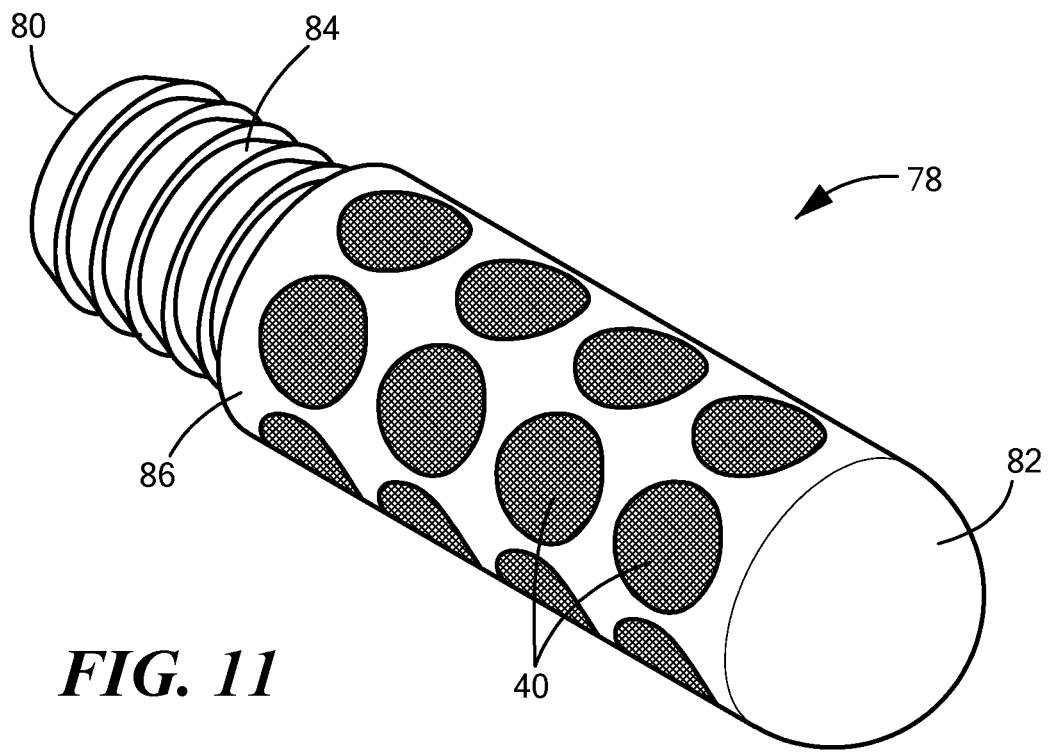
FIG. 11 shows a distal tip element.
Figure 12:
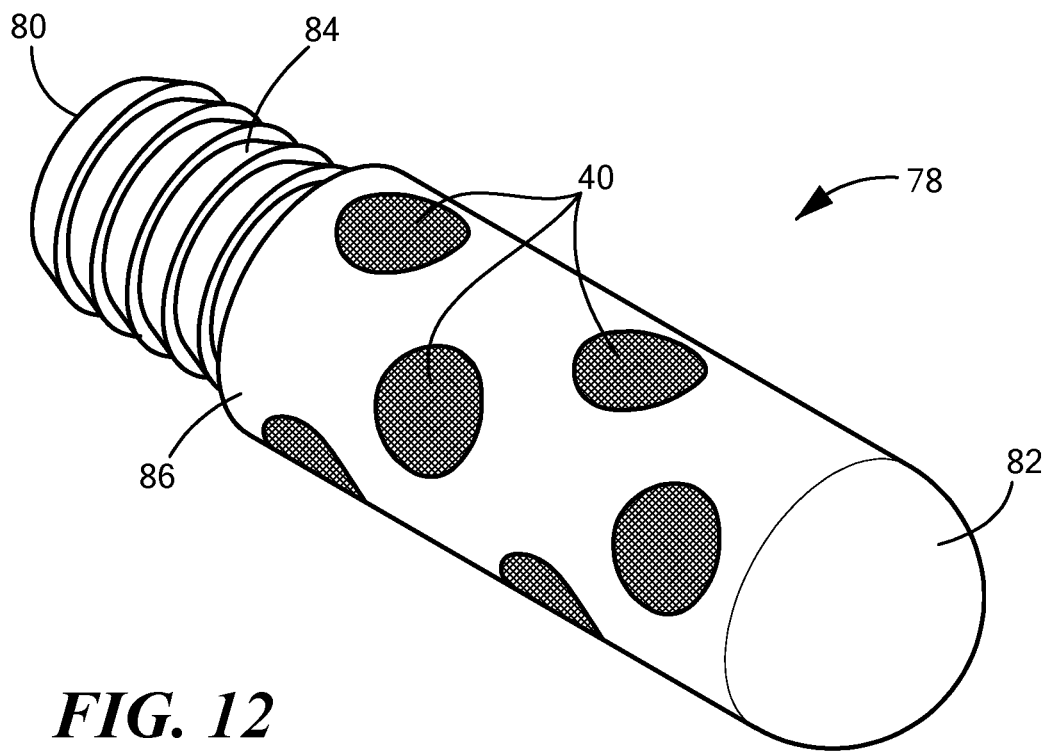
FIG. 12 shows a further embodiment of a distal tip element.

Referring now to FIGS. 11 and 12, embodiments of a distal tip element are shown. The distal tip element 78 may be a device component that is sized and configured to be attached to the elongate body distal portion 28. For example, the distal tip element 78 may include a first end 80 and a second end 82, and the first end 80 may include a barbed stem 84 that can be inserted into the distal end of the elongate body 22. The second end 80 of the distal tip element 78 may be rounded or have another atraumatic shape. The body 86 of the distal tip element 78 may be composed of the same material as the barbed stem 84, or the barbed stem 84 may be composed of a material with a higher durometer (or lower flexibility) than the body 86. The material of at least the body 86 may be selected to provide the body 86 with a desired flexibility to allow it to conform to irregular tissue surfaces. As a non-limiting example, the body 86 may be composed of nylon, polyurethane, and/or polydimethylsiloxane (PDMS, also referred to as silicone).

The distal tip element 78 may have one or more areas of a conductive material, such as metal nanoparticles as discussed above. The areas of conductive material may be used as mapping electrodes 40, although they may also be used as navigation electrodes, impedance measurement electrodes, and/or treatment electrodes, due to their enhanced thermal conductivity. In the embodiment shown in FIG. 10, the electrodes 40 have a grid-like spacing, with all electrodes being aligned both along the length of elongate body 28 and around the circumference of the elongate body 28. In the additional embodiment shown in FIG. 12, the electrodes have an offset spacing. Although the distal tip element 78 is shown in FIGS. 11 and 12 as having a plurality of discrete, round electrodes 40, it will be understood that the areas of conductive material may be of any number, size, or configuration, including, but not limited to, linear, zigzag, serpentine, winding, or the like. Optionally, the rounded second end 82 of the distal tip element 78 may also include the conductive material to provide the device with a distal tip electrode.

It will be appreciated by persons skilled in the art that the present embodiments are not limited to what has been particularly shown and described herein above. In addition, unless mention was made above to the contrary, it should be noted that all of the accompanying drawings are not to scale.

A variety of modifications and variations are possible in light of the above teachings without departing from the scope of the following claims.

What is claimed is:

1. A medical device comprising:
an elongate body having a proximal portion and a distal portion, the distal portion having: an interior surface and an exterior surface opposite of the interior surface; and the distal portion being transitionable between a first substantially linear configuration and a second configuration, the second configuration being selected from the group consisting of a curvilinear, a looped, and an expanded configuration; and
a detachable distal tip element attached to the distal portion of the elongate body including:
  a body having an elongated cylindrical dome shape formed by nylon, polyurethane, and/or polydimethylsiloxane and having a first flexibility;
  a barbed stem proximal to the body and configured to be received within the distal portion of the elongate body, the barbed stem being composed of a second material different than the first material with a lower flexibility than the first material; and
  at least one mapping element comprising thermally conductive nanoparticles integrated and coplanar with an outer surface of the body such that the at least one mapping element does not protrude beyond the outer surface of the body and the at least one mapping element has a flexibility or compliance that is at least substantially the same as the flexibility or compliance of the body.

2. The medical device of claim 1, wherein the metallic nanoparticles are composed of at least one of platinum and platinum-iridium.

3. The medical device of claim 1, wherein the elongate body comprises a mapping element comprising thermally conductive material.

4. The medical device of claim 3, wherein the detachable distal tip element has a circumference, each of the at least one mapping elements extending around less than an entirety of the circumference.

5. A medical system comprising:
a medical device comprising:
  an elongate body having a proximal portion and a distal portion, the distal portion having: an interior surface and an exterior surface opposite of the interior surface; and the distal portion being transitionable between a first substantially linear configuration and a second configuration, the second configuration being selected from the group consisting of a curvilinear, a looped, and an expanded configuration; and
  a detachable distal tip element attached to the distal portion of the elongate body including:
    a body having an elongated cylindrical dome shape formed by nylon, polyurethane, and/or polydimethylsiloxane and having a first flexibility;
    a barbed stem proximal to the body and configured to be received within the distal portion of the elongate body, the barbed stem being composed of a second material different than the first material with a lower flexibility than the first material; and
    at least one mapping element comprising thermally conductive nanoparticles integrated and coplanar with an outer surface of the body such that the at least one mapping element does not protrude beyond the outer surface of the body and the at least one mapping element has a flexibility or compliance that is at least substantially the same as the flexibility or compliance of the body; and
a control unit in communication with the medical device.

6. The medical system of claim 5, wherein the detachable distal tip element has a circumference, each of the at least one mapping elements extending around less than an entirety of the circumference.

7. The medical system of claim 6, wherein the at least one mapping element includes a plurality of mapping electrodes spaced apart from each other and extending along a distance of the elongate body in a distal-to-proximal direction.

8. A medical system comprising:
a medical device comprising:
  an elongate body having an inner surface and an exterior surface opposite the inner surface, the elongate body further having an at least substantially continuous circumference, the elongate body being transitionable between a first substantially linear configuration and a second configuration, the second configuration being selected from the group consisting of a curvilinear, a looped, and an expanded configuration;
  a detachable distal tip element attached to the distal portion of the elongate body including:
    a body having an elongated cylindrical dome shape formed by nylon, polyurethane, and/or polydimethylsiloxane and having a first flexibility;
    a barbed stem proximal to the body and configured to be received within a distal portion of the elongate body, the barbed stem being composed of a second material different than the first material with a lower flexibility than the first material; and
    a plurality of electrodes on the body that are configured to record at least one impedance measurement, the plurality of electrodes being integrated and coplanar with an outer surface of the body such that the plurality of electrodes do not protrude beyond the outer surface of the body, each of the plurality of electrodes being an area of thermally conductive nanoparticles composed of at least one of platinum, and platinum-iridium, each of the plurality of electrodes extending around less than an entirety of the circumference of the body and the at least one mapping element has a flexibility or compliance that is at least substantially the same as the flexibility or compliance of the body; and
a control unit in communication with the medical device and configured to receive the at least one impedance measurement from the plurality of electrodes and to assess a formation of a lesion in an area of tissue based on the at least one impedance measurement.

* * * * *